United States Patent [19]

Suh

[11] 4,073,798
[45] Feb. 14, 1978

[54] PREPARATION OF ETHYLAMINE DERIVATIVES

[75] Inventor: John T. Suh, Mequon, Wis.

[73] Assignee: Nicholas International Limited, Australia

[21] Appl. No.: 743,400

[22] Filed: Nov. 19, 1976

[30] Foreign Application Priority Data

Nov. 27, 1975  United Kingdom .............. 48709/75

[51] Int. Cl.$^2$ .......................................... C07D 317/44
[52] U.S. Cl. ............................................. 260/340.5 R
[58] Field of Search ................... 260/340.5, 570.8 R, 260/583 M

[56] References Cited

U.S. PATENT DOCUMENTS

| | | | |
|---|---|---|---|
| 2,420,382 | 5/1947 | Robertson | 260/570.8 R |
| 3,448,106 | 6/1969 | Nickl et al. | 260/340.5 R |
| 3,546,297 | 12/1970 | Kosak et al. | 260/570.8 R |

*Primary Examiner*—Ethel G. Love
*Attorney, Agent, or Firm*—Foster York

[57] ABSTRACT

A process for preparing a compound of the formula

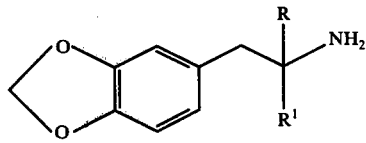

wherein R and $R^1$ independently are selected from hydrogen and $C_1$–$C_4$ alkyl groups, which comprises catalytically hydrogenating a compound of formula

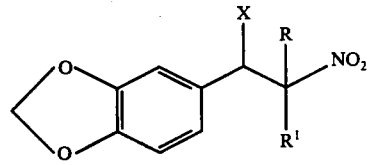

wherein R and $R^1$ are as defined above and X is halogen using platinum oxide as catalyst.

4 Claims, No Drawings

PREPARATION OF ETHYLAMINE DERIVATIVES

The present invention relates to a process for preparing ethylamine derivatives.

The invention provides a process for preparing compounds of formula I

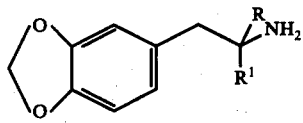

(wherein R and R¹ independently represent hydrogen or C₁-C₄ alkyl) which comprises catalytically hydrogenating a compound of formula IV

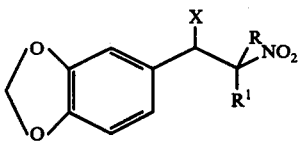

(wherein R and R¹ are as defined above and X is halogen) using platinum oxide as catalyst.

The hydrogenation step of the above process is preferably carried out at super-atmospheric pressures and at elevated temperatures typically at pressures of about 1000 p.s.i. and at about 100° C. The yield in the hydrogenation step is usually in the range 63–95% when platinum oxide is used as catalyst and both dehalogenation and reduction of the compound of formula (IV) can be achieved in a single step whereas other catalysts based, for example, on palladium or nickle have been found to give unsatisfactory yields (20–35%) and to give products which are heavily contaminated with various undesirable by-products.

The compounds of formula IV can be prepared by halogenating a compound of formula III

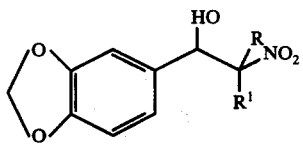

wherein R and R¹ independently represent hydrogen or C₁-C₄ alkyl).

The compounds of formula III can be prepared by treating piperonal or a functional derivative thereof with a compound of the formula II

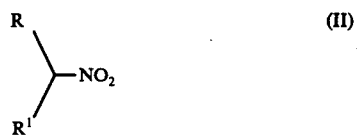

(wherein R and R¹ independently represent hydrogen or C₁-C₄ alkyl.

The preparation of the compound 1,1-dimethyl-2-(3,4-methylenedioxyphenyl)ethylamine is illustrated in the following reaction scheme:

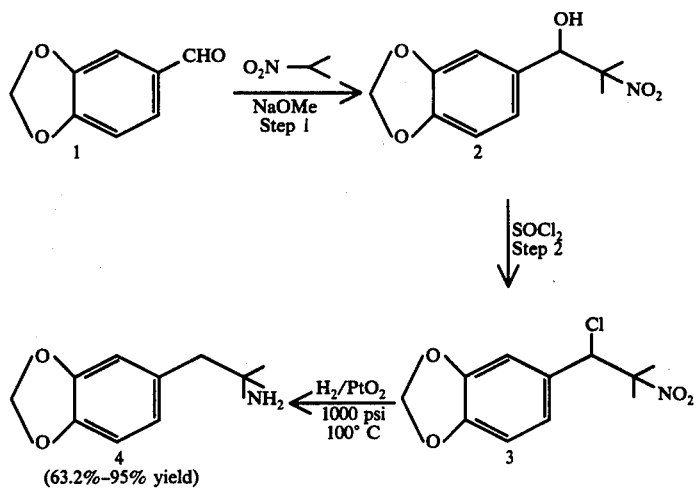

(63.2%–95% yield)

The compounds produced according to the invention are useful as intermediates in the preparation of the pharmaceutically useful (bronchodilator) compounds described and claimed in U.S. Pat. Nos. 3,700,692 and 3,786,154 and U.K. Pat. No. 1,358,005.

The invention is illustrated in the following Example:

EXAMPLE

Preparation of 1,1-Dimethyl-2-(3,4-methylenedioxyphenyl)ethylamine a. 1,1-Dimethyl-2-hydroxy-2-(3,4-methylenedioxyphenyl)nitroethane A solution of 55.2 g (2.4 g atom) of sodium in 2.62 liters of methanol cooled to 25° C was added to 684 g (689.5 ml; 7.68 moles) of 2-nitropropane after which 360.4 g (2.4 moles) of piperonal were added. The solution was stirred at room temperature for 18 hours, cooled in an ice bath and acidified with 2.4 liters of 1N sulphuric acid. The resulting mixture was diluted with 5 liters of water, and an oil which precipitated was syphoned off and added to a rapidly stirred solution of 187.4 g (1.8 moles) of sodium bisulphate in 1.2 liters of water. The mixture was stirred for 15 minutes, after which the solid formed was separated and washed three times with ether. The organic layer was separated off, washed with brine, dried and concentrated to an oil which was crystallised from a mixture of 250 ml of toluene and 850 ml of hexane to give 1,1-dimethyl-2-hydroxy-2-(3,4-methylenedioxyphenyl)nitroethane m.p. 88°–91° (Yield 200.4 g). The mother liquor from the crystallisation was diluted with a further liter of hexane to give a further crop of the product, m.p. 88°–91° (49.9 g; total yield 250.3 g, 43.6%).

b. 1,1-Dimethyl-2-chloro-2-(3,4-methylenedioxyphenyl)nitroethane

A solution of 242.8 g (1.016 moles) of 1,1-dimethyl-2-hydroxy-2-(3,4-methylenedioxyphenyl)nitroethane in 500 ml of benzene was treated with 139 g (84 ml, 1.17 moles) of thionyl chloride, after which the mixture was refluxed for 4 hours, cooled slightly and concentrated to a dark yellow oil which crystallised on cooling and seeding. The resulting solid was broken up and dispersed in 150 ml of 2-propanol after which it was separated, washed twice with cold 2-propanol and dried to give crude 1,1-dimethyl-2-chloro-2-(3,4-methylenedioxyphenyl)nitroethane as a light yellow solid, m.p. 63°–66° C (Yield 230.9 g). A 201.3 g portion of the crude product was treated with "Darco" (Trade Mark) and recrystallised from 402 ml of SDA-30 to give 181.6 g (79.6%) of the pure product as a white solid, m.p. 65°–67° C.

c. 1,1-Dimethyl-2-(3,4-methylenedioxypenyl)ethylamine

A mixture of 51.52 g (0.2 mole) of 1,1-dimethyl-2-chloro-2-(3,4-methylenedioxyphenyl)nitroethane, 2.0 g of 83.8 weight % purity platinum oxide, 18.0 g (0.22 mole) of sodium acetate and 4.0 g of "Darco" in 96 ml of acetic acid and 500 ml of SDA-30 was stirred under a hydrogen atmosphere at 1000 p.s.i. and 100° C for a period of 5 hours, after which uptake of hydrogen ceased. The solution was cooled and filtered, and the filtrate was concentrated to an oil which was treated with 400 ml of water. The mixture was extracted twice with ether, after which the aqueous layer was made alkaline by addition of 20% aqueous sodium hydroxide and extracted four times with chloroform. The combined extracts were filtered through "Dicalite" (Trade Mark), washed with water, dried and concentrated to a light yellow oil which was distilled using a 2" 19.38 distillation column to give 1,1-dimethyl-2-(3,4-methylenedioxyphenyl)ethylamine as a clear colourless oil, b.p. 68°–85° C, 0.06–0.04 mm Hg (Yield 24.4 g, 63.2%)

ANALYSIS

Calculated for $C_{11}H_{15}NO_2$: C, 68.37%; H, 7.82%; N, 7.25%. Found: C, 68.15%; H, 7.16%; N, 7.16%.

Processes for using the compounds of formula I as intermediates in the production of the bronchodilator compounds which are described and claimed in U.S. Pat. Nos. 3,700,692 and 3,786,154 and United Kingdom Patent 1,358,003 are disclosed in the United States application of John T. Suh and Thomas M. Bare entitled "Process for Preparing Aminoethanols" filed on the same date as the instant U.S. application. The said U.S. application of Suh and Bare is hereby incorporated by reference. Particular attention is directed to the following portions of the referenced application (formula IIB of the referenced application being the same as formula I of the instant application):

United States Pat. Nos. 3,700,692 and 3,786,154 and U.K. Pat. No. 1,358,005 claim certain aminoethanols of the formula I

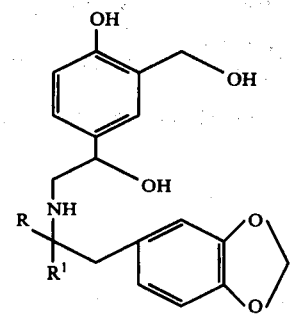

wherein R and $R^1$ each independently represent hydrogen or a $C_1$–$C_4$ alkyl group. The compounds of formula I can exist in the form of acid addition salts; for example they can be in the form of their nitrate, sulphate or hydrochloride. The compounds of formula I have been found in preliminary screening tests to be orally effective bronchodilators which produce a more potent and sustained bronchodilation than isoproterenol while having less undesirable side effects on the contractile forces and heart rates of test animals than does isoproterenol.

We have now discovered an improved process for preparing the compounds of formula I which comprises reacting a compound of formula IIA

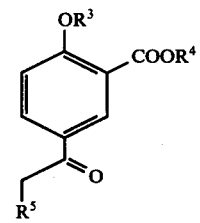

(wherein $R^3$ represents a protecting group for an aromatic hydroxyl function; $R^4$ represents an alkyl group, e.g., a methyl group, ethyl group, n-propyl group, isopropyl or a butyl group; and $R^5$ represents a halogen atom) in an appropriate solvent with a compound of formula IIB

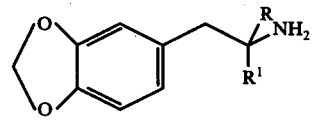

(wherein R and $R^1$ have the meanings previously given) to give a compound of formula III

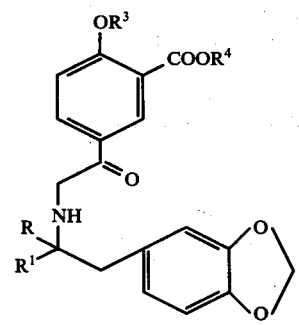

(wherein R, R¹, R³ and R⁴ have the meanings previously given), reducing the compound of formula III to obtain a compound of formula IV

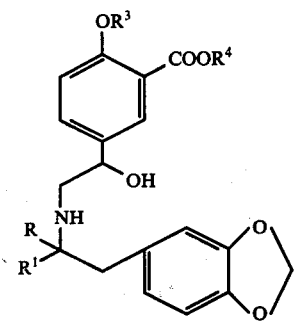

(IV)

(wherein R, R¹, R³ and R⁴ have the meanings previously defined); reducing the compound of formula IV to give a compound of formula V

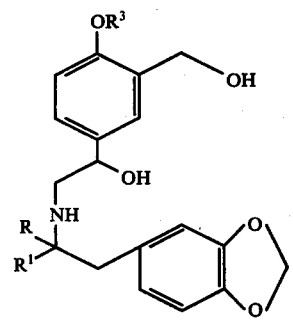

(V)

(wherein R, R¹ and R³ have the meanings previously given); removing the protecting group R³ to give a compound of formula I, and if desired converting the compound of formula I to a salt by reaction with an appropriate acid.

The reaction between the compound of formula IIA and the compound of formula IIB can conveniently be carried out in an inert polar solvent such as tetrahydrofuran. When the group R⁴ in the product of formula IV is a methyl group it is preferably converted into a branched chain alkyl group such as an isopropyl group which is more readily reactable with a metal hydride. The conversion can be carried out by refluxing the compound of formula IV in the appropriate alcohol in the presence of an alkali metal borohydride such as sodium borohydride. The compound of formula IV is then reduced to the compound of formula V by metal hydride reduction (see H.O. House, Modern Synthetic Reactions, W. A. Benjamin Inc. 1965 at Chapter 2) after which the resulting mixture is treated with water and the compound of formula V is isolated. The protecting group $R^3$ is then removed by conventional means, for example when (as is preferred) $R^3$ is a benzyl group by catalytic hydrogenation using palladium on charcoal, after which the resulting compound of formula I can if desired be converted into an acid addition salt by treatment with an acid, for example sulphuric acid, hydrochloric acid or nitric acid.

I claim:

1. A process for preparing a compound of formula I

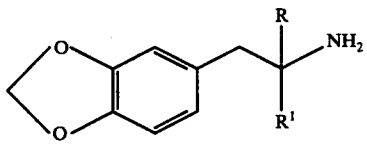

wherein R and $R^1$ independently are selected from hydrogen and $C_1$-$C_4$ alkyl groups, which comprises catalytically hydrogenating under super-atmospheric pressure and at above ambient temperature a compound of formula (IV)

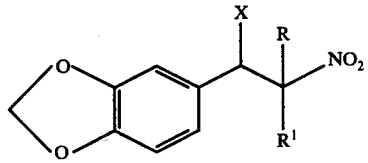

wherein R and $R^1$ are defined above and X is halogen using platinum oxide as catalyst.

2. The process according to claim 1 wherein said hydrogenation is carried out at a pressure of about 1000 psi and at a temperature of about 100° C.

3. The process according to claim 1 wherein R and $R^1$ are both methyl.

4. The process according to claim 1 wherein X is chlorine.

* * * * *